US008556824B2

(12) United States Patent
Xu et al.

(10) Patent No.: US 8,556,824 B2
(45) Date of Patent: Oct. 15, 2013

(54) PRODUCTION OF OPTICAL PULSES AT A DESIRED WAVELENGTH USING SOLITON SELF-FREQUENCY SHIFT

(75) Inventors: Chris Xu, Ithaca, NY (US); James Van Howe, Davenport, IA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 828 days.

(21) Appl. No.: 12/446,617

(22) PCT Filed: Oct. 26, 2007

(86) PCT No.: PCT/US2007/082623
§ 371 (c)(1),
(2), (4) Date: Dec. 14, 2009

(87) PCT Pub. No.: WO2008/052153
PCT Pub. Date: May 2, 2008

(65) Prior Publication Data
US 2010/0100006 A1    Apr. 22, 2010

Related U.S. Application Data

(60) Provisional application No. 60/863,082, filed on Oct. 26, 2006, provisional application No. 60/896,357, filed on Mar. 22, 2007.

(51) Int. Cl.
*A61B 10/00* (2006.01)
*A61B 1/06* (2006.01)
*A61B 18/18* (2006.01)

(52) U.S. Cl.
USPC .............................. 600/562; 600/182; 606/15

(58) Field of Classification Search
USPC ...................... 600/562, 342; 385/37, 123, 125
See application file for complete search history.

(56) References Cited

U.S. PATENT DOCUMENTS

| 6,445,939 | B1 | 9/2002 | Swanson et al. |
| 2002/0168161 | A1 | 11/2002 | Price et al. |
| 2005/0163426 | A1 | 7/2005 | Fermann et al. |

OTHER PUBLICATIONS

Jespersen et al.; A higher-order-mode fiber delivery for Ti: Sapphire femtosecond lasers; Apr. 12, 2010; vol. 18, No. 8; Optics Express; 7798-7806.

*Primary Examiner* — Brian Szmal
*Assistant Examiner* — Fangemonique Smith
(74) *Attorney, Agent, or Firm* — William Greener; Bond, Schoeneck & King, PLLC

(57) ABSTRACT

The present invention relates to an apparatus for producing optical pulses of a desired wavelength. The apparatus includes an optical pulse source operable to generate input optical pulses at a first wavelength. The apparatus further includes a higher order mode (HOM) fiber module operable to receive the input optical pulses at the first wavelength, and thereafter to produce output optical pulses at the desired wavelength by soliton self-frequency shift (SSFS). The present invention also relates to a method of producing optical pulses having a desired wavelength. This method includes generating input optical pulses using an optical pulse source, where the input optical pulses have a first wavelength and a first spatial mode. The input optical pulses are delivered into an HOM fiber module to alter the wavelength of the input optical pulses from the first wavelength to a desired wavelength by soliton self-frequency shift (SSFS) within the HOM fiber module, thereby producing output optical pulses having the desired wavelength.

49 Claims, 6 Drawing Sheets

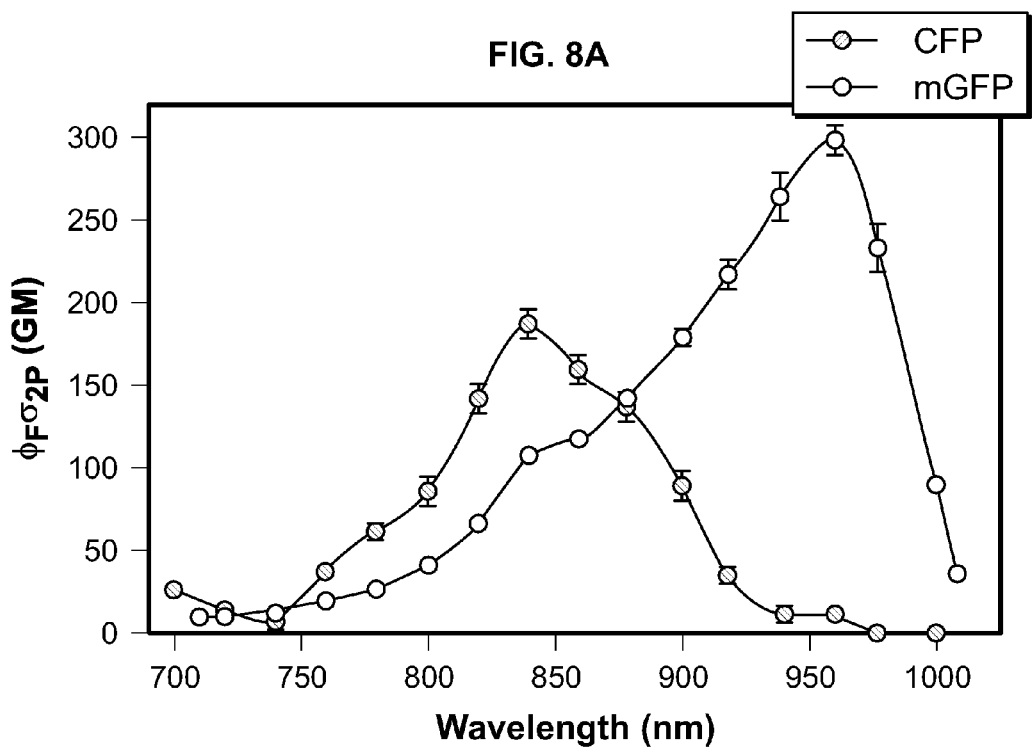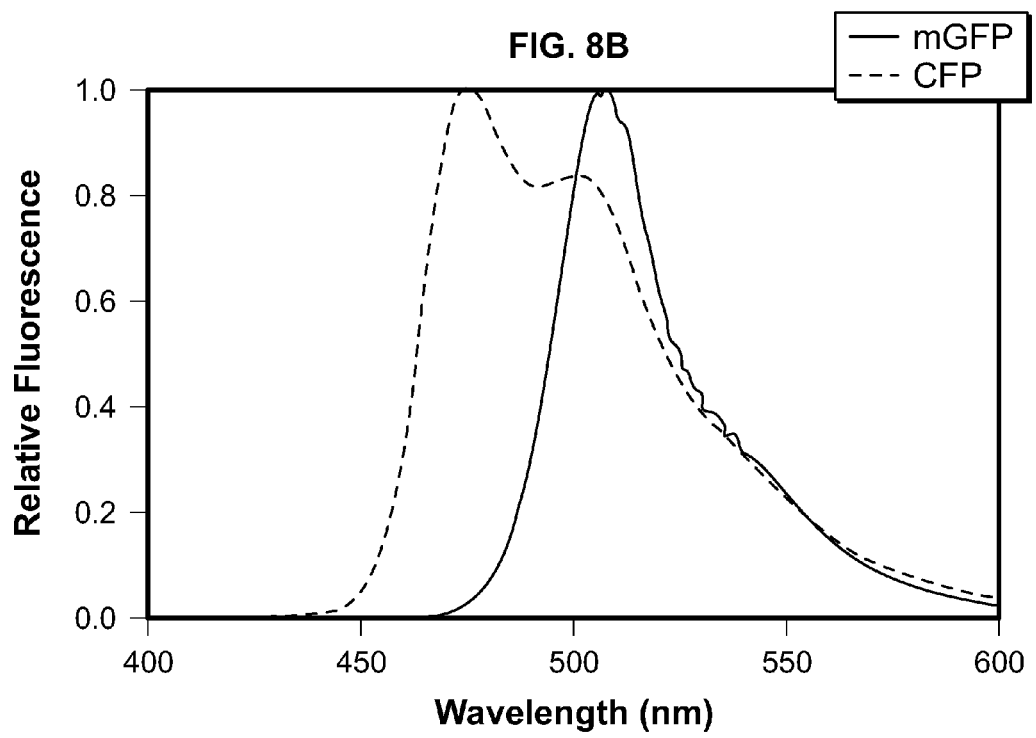

PRODUCTION OF OPTICAL PULSES AT A DESIRED WAVELENGTH USING SOLITON SELF-FREQUENCY SHIFT

RELATED APPLICATION

This application claims benefit of U.S. Provisional Application No. 60/863,082 filed Oct. 26, 2006 and U.S. Provisional Application No. 60/896,357 filed Mar. 22, 2007, which are hereby incorporated by reference.

FIELD OF THE INVENTION

The present invention relates to the production of optical pulses at a desired wavelength using soliton self-frequency shift in higher order mode fibers.

BACKGROUND OF THE INVENTION

The phenomenon of soliton self-frequency shift (SSFS) in optical fiber in which Raman self-pumping continuously transfers energy from higher to lower frequencies (Dianov et al., *JETP. Lett.* 41:294 (1985)) has been exploited over the last decade in order to fabricate widely frequency-tunable, femtosecond pulse sources with fiber delivery (Nishizawa et al., *IEEE Photon. Technol. Lett.* 11:325 (1999); Fermann et al., *Opt. Lett.* 24:1428 (1999); Liu et al., *Opt. Lett.* 26:358 (2001); Washburn et al., *Electron. Lett.* 37:1510 (2001); Lim et al., *Electron. Lett.* 40:1523 (2004); Luan et al., *Opt. Express* 12:835 (2004). Because anomalous (positive) dispersion ($\beta_2 < 0$ or $D > 0$) is required for the generation and maintenance of solitons, early sources which made use of SSFS for wavelength tuning were restricted to wavelength regimes greater than 1300 nm where conventional silica fibers exhibited positive dispersion (Nishizawa et al., *IEEE Photon. Technol. Lett.* 11:325 (1999); Fermann et al., *Opt. Lett.* 24:1428 (1999)). The recent development of index-guided photonic crystal fibers (PCF) and air-core photonic band-gap fibers (PBGF) relaxed this requirement with the ability to design large positive waveguide dispersion and therefore large positive net dispersion in optical fibers at nearly any desired wavelength (Knight et al., *IEEE Photon. Technol. Lett.* 12:807 (2000)). This allowed for a number of demonstrations of tunable SSFS sources supporting input wavelengths as low as 800 nm in the anomalous dispersion regime (Liu et al., *Opt. Lett.* 26:358 (2001); Washburn et al., *Electron. Lett.* 37:1510 (2001); Lim et al., *Electron. Lett.* 40:1523 (2004); Luan et al., *Opt. Express* 12:835 (2004)).

Unfortunately, the pulse energy required to support stable Raman-shifted solitons below 1300 nm in index-guided PCFs and air-core PBGFs is either on the very low side, a fraction of 1 nJ for silica-core PCFs, (Washburn et al., *Electron. Lett.* 37:1510 (2001); Lim et al., *Electron. Lett.* 40:1523 (2004)) or on the very high side, greater than 100 nJ (requiring an input from an amplified optical system) for air-core PBGFs (Luan et al., *Opt. Express* 12:835 (2004)). The low-energy limit is due to high nonlinearity in the PCF. In order to generate large positive waveguide dispersion to overcome the negative dispersion of the material, the effective area of the fiber core must be reduced. For positive total dispersion at wavelengths less than 1300 nm this corresponds to an effective area, $A_{eff}$, of 2-5 $\mu m^2$, approximately an order of magnitude less than conventional single mode fiber (SMF). The high-energy limit is due to low nonlinearity in the air-core PBGF where the nonlinear index, $n_2$, of air is roughly 1000 times less than that of silica. These extreme ends of nonlinearity dictate the required pulse energy (U) for soliton propagation, which scales as U·D·$A_{eff}$/$n_2$. In fact, most microstructure fibers and tapered fibers with positive dispersion are intentionally designed to demonstrate nonlinear optical effects at the lowest possible pulse energy, while air-core PBGFs are often used for applications that require linear propagation, such as pulse delivery. For these reasons, previous work using SSFS below 1300 nm were performed at soliton energies either too low or too high (by at least an order of magnitude) for many practical applications, such as multiphoton imaging where bulk solid state lasers are currently the mainstay for the excitation source (Diaspro, A., *Confocal and Two-Photon Microscopy*, Wiley-Liss: New York (2002)).

Applications of Femtosecond Sources in Biomedical Research.

There are a number of biomedical applications that require femtosecond sources. Although applications requiring a large spectral bandwidth (such as optical coherence tomography) can also be performed using incoherent sources such as superluminescent diodes, techniques based on nonlinear optical effects, such as multiphoton microscopy and endoscopy, almost universally require the high peak power generated by a femtosecond source.

Endoscopes play an important role in medical diagnostics by making it possible to visualize tissue at remote internal sites in a minimally invasive fashion. The most common form employs an imaging fiber bundle to provide high quality white light reflection imaging. Laser scanning confocal reflection and fluorescence endoscopes also exist and can provide 3D cellular resolution in tissues. Confocal endoscopes are now becoming available commercially (Optiscan Ltd, Australia, Lucid Inc, Rochester) and are being applied in a number of clinical trials for cancer diagnosis. Multiphoton excitation based endoscopes has attracted significant attention recently. There were a number of advances, including fiber delivery of excitation pulses, miniature scanners, double clad fibers for efficient signal collections, etc. Thus, just like multiphoton microscopes have proven to be a powerful tool in biological imaging, multiphoton endoscopes have great potentials to improve the capability of the existing laser-scanning optical endoscopes. It is quite obvious that a compact, fully electronically controlled, femtosecond system seamlessly integrated with fiber optic delivery is essential for multiphoton endoscopy in medical diagnostics, particularly to biomedical experts who are not trained in lasers and optics.

Perhaps the most promising and successful area in biomedical imaging that showcases the unique advantage of multiphoton excitation is imaging deep into scattering tissues. In the past 5 to 10 years, multiphoton microscopes have greatly improved the penetration depth of optical imaging and proven to be well suited for a variety of imaging applications deep within intact or semi-intact tissues, such as demonstrated in the studies of neuronal activity and anatomy, developing embryos, and tissue morphology and pathology. When compared to one-photon confocal microscopy, a factor of 2 to 3 improvement in penetration depth is obtained by multiphoton microscopes. Nonetheless, despite the heroic effort of employing energetic pulses (~$\mu J$/pulse) produced by a regenerative amplifier, multiphoton microscopes have so far been restricted to less than 1 mm in penetration depth. One promising direction for imaging deep into scattering tissue is to use longer excitation wavelength. Although the "diagnostic and therapeutic window," which is in between the absorption regions of the intrinsic molecules and water, extends all the way to approximately 1300 nm, previous investigations involving multiphoton imaging are almost exclusively carried out within the near IR spectral window of approximately 0.7 to 1.1 $\mu m$, constrained mostly by the availability of the excitation source. Currently, there are only two femtosecond sources at the spectral window of 1200 to 1300 nm, the Cr:Forsterite laser and the optical parametric oscillator (OPO) pumped by a femtosecond Ti:Sapphire (Ti:S) laser. In terms of robustness and easy operation, both sources rank significantly below the Ti:S laser. Thus, the development of a reliable fiber source tunable from 1030 to 1280 nm will open up new opportunities for biomedical imaging, particularly for applications requiring deep tissue penetration.
Femtosecond Sources for Multiphoton Imaging.

Shortly after the inception of multiphoton microscopes, mode-locked solid state femtosecond lasers, most commonly the Ti:S lasers, have emerged as the favorite excitation sources to dominate the multiphoton microscope field today. When compared to earlier ultrafast lasers, e.g., ultrafast dye lasers, the Ti:S lasers are highly robust and flexible. The concurrent development of the mode-locked Ti:S lasers was perhaps the biggest gift for multiphoton microscopes and enabled them to rapidly become a valuable instrument for biological research. Nonetheless, the cost, complexity, and the limited potential for integration of the bulk solid state lasers have hampered the widespread applications of multiphoton microscopes in biological research. The fact that a disproportionate number of multiphoton microscope systems are located in physics and engineering departments, instead of the more biologically oriented institutions, reflects at least in part the practical limitations of the femtosecond pulsed source. Obviously, the requirement of a robust, fiber delivered, and cheap source is even more urgent for multiphoton endoscopy in a clinical environment.

Mode-locked femtosecond fiber lasers at 1.03 and 1.55 µm have been improving significantly in the last several years, mainly in the output pulse energy (from 1 to ~10 nJ). Even higher pulse energy can be achieved in femtosecond fiber sources based on fiber chirped pulse amplification. However, femtosecond fiber sources, including lasers and CPA systems, have seen only limited applications in multiphoton imaging. The main reason is that they offer very limited wavelength tunability (tens of nanometers at best), severely restricting the applicability of these lasers, making them only suitable for some special purposes. In addition, existing femtosecond fiber sources at high pulse energy (>1 nJ) are not truly "all fiber," i.e., the output are not delivered through a single mode optical fiber. Thus, additional setup, typically involving free-space optics, must be used to deliver the pulses to the imaging apparatus, partially negating the advantages of the fiber source. Reports have demonstrated the possibility of propagating femtosecond IR pulses through a large core optical fiber at intensities high enough (~1 nJ) for multiphoton imaging. In addition, a special HOM fiber that is capable of delivery energetic femtosecond pulses (~1 nJ) has been demonstrated. However, both fibers have normal dispersion, and both require a free-space grating pair for dispersion compensation. Not only is such a grating pair lossy and complicated to align, it needs careful adjustment for varying fiber length, output wavelength, and output pulse energy, and falls short of the requirement for most biomedical research labs and future clinical applications.

The present invention is directed to overcoming these and other deficiencies in the art.

SUMMARY OF THE INVENTION

The present invention relates to an apparatus for producing optical pulses of a desired wavelength. The apparatus includes an optical pulse source operable to generate input optical pulses at a first wavelength. The apparatus further includes a higher order mode (HOM) fiber module operable to receive the input optical pulses at the first wavelength, and thereafter to produce output optical pulses at the desired wavelength by soliton self-frequency shift (SSFS).

The present invention also relates to a method of producing optical pulses having a desired wavelength. This method includes generating input optical pulses using an optical pulse source, where the input optical pulses have a first wavelength and a first spatial mode. The input optical pulses are delivered into an HOM fiber module to alter the wavelength of the input optical pulses from the first wavelength to a desired wavelength by soliton self-frequency shift (SSFS) within the HOM fiber module, thereby producing output optical pulses having the desired wavelength.

The present invention is useful in providing optical pulses that are tunable over a wide wavelength range. The present invention can be used in any application that involves optical pulses. Examples of such uses include, without limitation, spectroscopy, endoscopy, and microscopy applications. Such uses can involve medical, diagnostic, and non-medical applications. In one embodiment, the present invention provides wavelength tunable, all-fiber, energetic femtosecond sources based on a new class of optical fiber (i.e., an HOM fiber) that was recently demonstrated, where, for the first time, a large anomalous dispersion was achieved at wavelengths below 1300 nm in an all-silica fiber.

Additional aspects will be apparent to those of ordinary skill in the art in view of the detailed description of various embodiments, which is made with reference to the drawings, a brief description of which is provided below.

BRIEF DESCRIPTION OF THE DRAWINGS

FIG. 8A shows a two-photon excitation spectra of CFP and monomeric eGFP, two common genetically encodable fluorescent proteins.

FIG. 8B shows emission spectra of the CFP and monomeric eGFP.

Figure 1A:
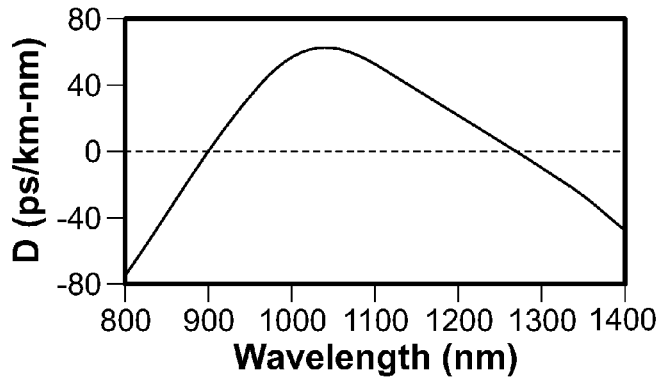
FIG. 1A is a graph of the total dispersion for propagation in the $LP_{02}$ mode.

While these examples are susceptible of embodiment in many different forms, there is shown in the drawings and will herein be described in detail preferred examples with the understanding that the present disclosure is to be considered as an exemplification and is not intended to limit the broad aspect to the embodiments illustrated.

DETAILED DESCRIPTION

One example described is an apparatus for producing optical pulses of a desired wavelength. The apparatus includes an optical pulse source operable to generate input optical pulses at a first wavelength. The apparatus further includes a higher order mode (HOM) fiber module operable to receive the input optical pulses at the first wavelength, and thereafter to produce output optical pulses at the desired wavelength by soliton self-frequency shift (SSFS).

In one embodiment, the HOM fiber module includes an HOM fiber. Suitable HOM fibers can include, without limitation, a solid silica-based fiber. In another embodiment, the HOM fiber module includes an HOM fiber and at least one mode converter. The at least one mode converter can be connectedly disposed between the optical pulse source and the HOM fiber. The HOM fiber module can also include an HOM fiber, a mode converter connectedly disposed between the optical pulse source and the HOM fiber, and also a second mode converter terminally connected to the HOM fiber. Suitable mode converters that can be used in the present invention are well known in the art, and can include, for example, a long period grating (LPG).

Suitable optical pulse sources that can be used in one example can include, without limitation, mode-locked lasers and chirped pulse amplification (CPA) systems. More particularly, the mode-locked laser can be a mode-locked fiber laser, and the CPA system can be a fiber CPA system. The optical pulse source used in the present invention can include those that generate input optical pulses having various pulse energies. In one embodiment, the optical pulse source generates a pulse energy of at least 1.0 nanojoule (nJ). In another embodiment, the optical pulse source generates input optical pulses having a pulse energy of between about 1.0 nJ and about 100 nJ.

The optical pulse source can also be one that generates input optical pulses such that the first wavelength is a wavelength within the transparent region of a silica-based fiber. In one embodiment, the optical pulse source is one that generates a first wavelength below 1300 nanometers (nm). In another embodiment, the optical pulse source is one that generates a first wavelength between the range of about 300 nm and about 1300 nm.

The optical pulse source used in the examples can also be one that generates input optical pulses having a subpicosecond pulse width.

Suitable HOM fiber modules that may be used can include, without limitation, HOM fibers that produce output optical pulses having a pulse energy of at least 1.0 nJ. Suitable HOM fiber modules can also be those that produce output optical pulses such that the desired wavelength is a wavelength within the transparent region of a silica-based fiber. In one embodiment, the HOM fiber module produces an output optical pulse having a desired wavelength that is below 1300 nm. In another embodiment, the HOM fiber module produces an output optical pulse having a desired wavelength between the range of about 300 nm and about 1300 nm. The HOM fiber module can also be such that it produces output optical pulses having a subpicosecond pulse width.

The apparatus can further include a power control system connectedly disposed between the optical pulse source and the HOM fiber module. The power control system for use in the present invention can be one that achieves subnanosecond power tuning of the optical input source at the first wavelength. Suitable power control systems can include, without limitation, a lithium niobate ($LiNbO_3$) intensity modulator device.

The apparatus can further include a single-mode fiber (SMF) connectedly disposed between the optical pulse source and the HOM fiber module.

The apparatus can be used in a variety of applications where optical pulses of a desired wavelength are needed. For example, the apparatus can be effective in producing output optical pulses that can penetrate animal or plant tissue at a penetration depth of at least 0.1 millimeters (mm).

The apparatus can further be such that the HOM fiber module is terminally associated with medical diagnostic tools such as an endoscope or an optical biopsy needle.

The apparatus can further be functionally associated with a multiphoton microscope system.

The apparatus can also further be functionally associated with a multiphoton imaging system.

The present invention also relates to a method of producing optical pulses having a desired wavelength. This method includes generating input optical pulses using an optical pulse source, where the input optical pulses have a first wavelength and a first spatial mode. The input optical pulses are delivered into an HOM fiber module to alter the wavelength of the input optical pulses from the first wavelength to a desired wavelength by soliton self-frequency shift (SSFS) within the HOM fiber module, thereby producing output optical pulses having the desired wavelength.

An example method can involve the use of the apparatus described herein as well as the various aspects and components of the apparatus (e.g., the optical pulse source and the HOM fiber module) described herein.

In one embodiment, the method can further include converting the first spatial mode of the input optical pulses into a second spatial mode prior delivering the input optical pulses into the HOM fiber so that the output optical pulses have the second spatial mode, where the first spatial mode and the second spatial mode are different modes. This method can further include reconverting the second spatial mode of the output optical pulses back to the first spatial mode.

In another embodiment, the method can further include tuning the wavelength of the optical pulses to a desired wavelength via the HOM fiber. The tuning can include, without limitation, power tuning. Such power tuning can include varying the power of the input optical pulses so as to vary the desired wavelength. In one embodiment, the power tuning can include subnanosecond power tuning using a power control system connectedly disposed between the optical pulse source and the HOM fiber module. Suitable power control systems can include, without limitation, a lithium niobate intensity modulator device. In another embodiment, the tuning can be achieved by varying the length of the HOM fiber so as to vary the desired wavelength.

Described in more detail below is the concept of SSFS in optical fibers and more particularly in HOM fibers.

Soliton Self-Frequency Shift in Optical Fibers.

Soliton Self-Frequency Shift (SSFS) is a well-known and well-understood phenomenon. Optical soliton pulses generally experience a continuous downshift of their carrier frequencies when propagating in a fiber with anomalous dispersion. This so-called soliton self-frequency shift originates from the intra-pulse stimulated Raman scattering which transfers the short wavelength part of the pulse spectrum toward the long wavelength part. Through the balancing of optical nonlinearity and fiber dispersion (i.e., a soliton condition), the pulse maintains its temporal and spectral profiles as it shifts to the longer wavelengths. The practical application of soliton self-frequency shift was limited because the use of conventional fibers for generating wavelength-shifting solitons. However, several new classes of optical fibers, such as photonic crystal fibers, sometimes also known as microstructure fiber and solid-core or air-core band gap fibers (BGF), has greatly improved the feasibility of SSFS. There are a number of experimental demonstrations of SSFS in PCF and BGF. However, none of the previous work can generate soliton energies that are of practical interest to biomedical research, i.e., solitons with pulse energies between 1 to 10 nJ and at wavelengths below 1300 nm. As explained above, the pulse energies produced in previous works are either one to two orders of magnitude too small or several orders of magnitude too large.

Because material nonlinearity for silica glass is positive at the relevant spectral range, the fundamental condition to form an optical soliton in silica fiber is anomalous dispersion. In addition, the existence of an optical soliton requires exact balance between fiber nonlinearity and dispersion. Thus, the energy of an optical soliton ($E_s$) is determined by material nonlinearity and dispersion, and scales as $$E_s \propto \lambda^3 \cdot D \cdot A_{eff}/n_2\tau. \quad (1),$$

where $n_2$ is the nonlinear refractive index of the material, $\tau$ is the pulse width, D is the dispersion parameter, $A_{eff}$ is the effective mode field area, and $\lambda$ is the wavelength. Although standard single mode fibers (SMF) cannot achieve anomalous dispersion at $\lambda$ less than 1280 nm, it was realized that the total dispersion (D) in a waveguide structure such as an optical fiber consists contributions from the material ($D_m$), the waveguide ($D_w$), and the bandgap (in the case of BGF). By appropriately engineering the contributions of the waveguide and/or the bandgap, it is possible to achieve anomalous dispersion (D>0) at virtually any wavelength, thus, enabling soliton and SSFS at wavelengths below 1280 nm. (It is worth noting that the dispersion parameter D is actually positive for anomalous dispersion.) Previously, there were two approaches to achieve anomalous dispersion, and therefore soliton propagation and SSFS, at $\lambda$<1280 nm:

(1) Small-core photonic crystal fibers can achieve anomalous dispersion for wavelengths down to approximately 550 nm. Large positive waveguide dispersion may be realised by tightly-confined $LP_{01}$ (fundamental) modes in PCFs. However, the associated trade-off is with $A_{eff}$, and designs that yield dispersion greater than +50 ps/nm/km in the wavelength ranges of 800 nm or 1030 nm typically have $A_{eff}$ of 2-5 $\mu m^2$. Because the soliton energy scales with the value of $D*A_{eff}$, a small $A_{eff}$ will severely limit the pulse energies that can be obtained with photonic crystal fibers. For example, in one experiment using a special PCF structure, a soliton pulse energy of approximately 20 pJ was obtained at 800 nm, orders of magnitude smaller than practical for imaging. Indeed, most photonic crystal fiber structures are designed to demonstrate nonlinear optical effects at the lowest possible pulse energy.

(2) Air-guided BGFs potentially can offer anomalous dispersion at any wavelength, but the extremely low nonlinearities in these fibers (the nonlinearity of air is ~one thousand times smaller than silica glass) make them impractical for a device that utilises a nonlinear interaction to achieve the frequency shift. In one demonstration, a MW (~$\mu$J pulse) optical amplifier is needed for observing SSFS in air-guiding fiber. Not only is such a high power unnecessary for most biomedical applications, the cost and complexity of the high power amplifier also makes it completely impractical as a tool for biomedical research.

Although SSFS provides a convenient mechanism for wavelength tuning of a fixed wavelength fiber laser, previous works in SSFS were performed at soliton energies either too low or too high (by at least an order of magnitude) for practical use. Thus, it is essential to develop a new fiber structure, with just the right amount of optical nonlinearity and dispersion (i.e., $D \cdot A_{eff}/n_2$) in order to produce wavelength tunable soliton pulses of practical utility for applications such as biomedical imaging.

Higher Order Mode (HOM) Fiber

The design freedoms enabled by HOM fibers may be used to achieve the desired soliton energy. For example, a higher order mode fiber may achieve anomalous dispersion at wavelengths below 1300 nm which is impossible to obtain in a conventional silica single mode fiber. A higher order mode fiber typically has a much larger effective area, $A_{eff}$ than that of a photonic crystal fiber for achieving higher soliton energy. The silica core of the HOM fiber retains just enough nonlinearity to make SSFS feasible at a practical energy level. Thus, an appropriately designed HOM fiber may provide the necessary characteristics desired for SSFS at a practical pulse energy of approximately 10 nJ.

Example Higher Order Mode (HOM) SSSF Based System

The example set forth below is for illustrative purposes only and are not intended to limit, in any way, the scope of the present invention.

In this example, soliton self-frequency shift from 1064 nm to 1200 nm with up to 57% power efficiency in a higher order mode (HOM) fiber is demonstrated (Ramachandran et al., *Opt. Lett.* 31:2532 (2006), which is hereby incorporated by reference in its entirety). This new class of fiber generates Raman solitons in intermediate energy regimes of 1 to 10 nJ pulses that cannot be reached through the use of PCFs and PBGFs. The HOM fiber used in this example exhibits large positive dispersion (~60 ps/nm-km) below 1300 nm while still maintaining a relatively large effective area of 44 $\mu m^2$ (Ramachandran et al., *Opt. Lett.* 31:2532 (2006), which is hereby incorporated by reference in its entirety), ten times that of index-guided PCFs for similar dispersion characteristics. Through soliton shaping and higher order soliton compression within the HOM fiber, clean 49 fs pulses from 200 fs input pulses were generated. Due to the dispersion characteristics of the HOM fiber, red-shifted Cherenkov radiation in the normal dispersion regime for appropriately energetic input pulses was also observed.

Figure 1B:
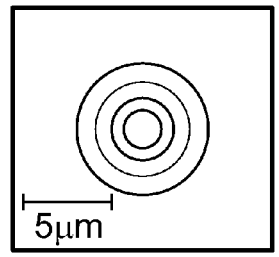
FIG. 1B is a near-field image of the $LP_{02}$ mode with an effective area, Aeff=44 µm$^2$.
Figure 1C:
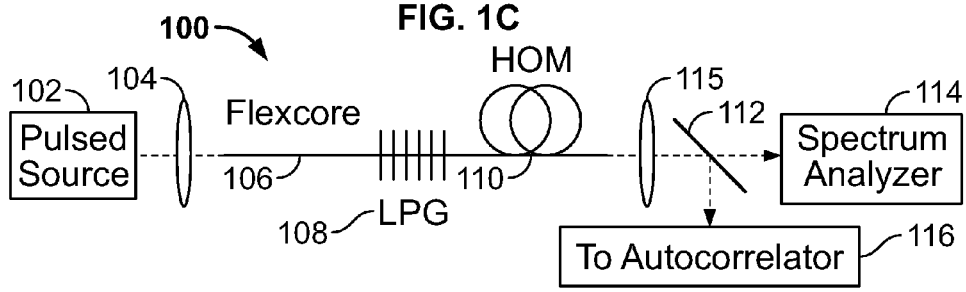
FIG. 1C is a block diagram of a measurement system used to demonstrate order mode fiber module.

FIG. 1A is a graph of the total dispersion for propagation in the $LP_{02}$ mode. FIG. 1B is a near-field image of the $LP_{02}$ mode with an effective area, Aeff=44 $\mu m^2$. FIG. 1C is a block diagram of a system 100 used to couple light through a higher order mode fiber module. To generate positive dispersion below 1300 nm while simultaneously maintaining a large effective area, light propagates solely in the $LP_{02}$ mode. Light is coupled into the $LP_{02}$ mode using a low-loss long period grating (LPG) (Ramachandran, S., *Journal of Lightwave Technology* 23:3426 (2005), which is hereby incorporated by reference in its entirety). The index profile of the HOM fiber is made such that the mode becomes more confined to the higher-index core with an increase in wavelength, resulting in net positive dispersion (Ramachandran et al., *Opt. Lett.* 31:2532 (2006), which is hereby incorporated by reference in its entirety). The graph in FIG. 1A shows a dispersion of 62.8 ps/nm-km at 1060 nm which is comparable to that of microstructured fibers used previously for SSFS (Liu et al., *Opt. Lett.* 26:358 (2001); Washburn et al., *Electron. Lett.* 37:1510 (2001); Lim et al., *Electron. Lett.* 40:1523 (2004), which are hereby incorporated by reference in their entirety), and exhibits two zero dispersion wavelengths at 908 nm and 1247 nm. The mode profile at the end face of the HOM fiber is shown in FIG. 1B, demonstrating a clean higher order $LP_{02}$ mode and an effective area of 44 μm². The system 100 in FIG. 1C includes a pulsed source 102, a coupling lens 104, a flexcore single mode fiber ("pigtail") 106, a long period grating 108, a higher order mode fiber 110, a splitter 112, a spectrum analyzer 114, a focusing lens 115 and an autocorrelator interface 116. In this example, light propagates in the fundamental mode through 12.5 cm of the standard single mode fiber 106 before being coupled into 1.0 m of the HOM fiber 110 with the 2.5 cm LPG 108 (entirely contained within a fiber fusion-splicing sleeve). Light resides in the $LP_{01}$ mode for approximately half the length of the grating 108 after which more than 99% is coupled into the $LP_{02}$ mode. The entire module has a total loss of 0.14 dB which includes all splices, fiber loss, and mode conversion. The all-silica HOM fiber 110 leverages the standard silica fiber manufacturing platform and retains the low loss properties (for both transmission and bending) of a conventional single mode fiber, allowing easy termination and splicing. The example HOM fiber module of the system 100 includes the single mode fiber 106, the LPG 108 and the HOM fiber 110.

Figure 2A:
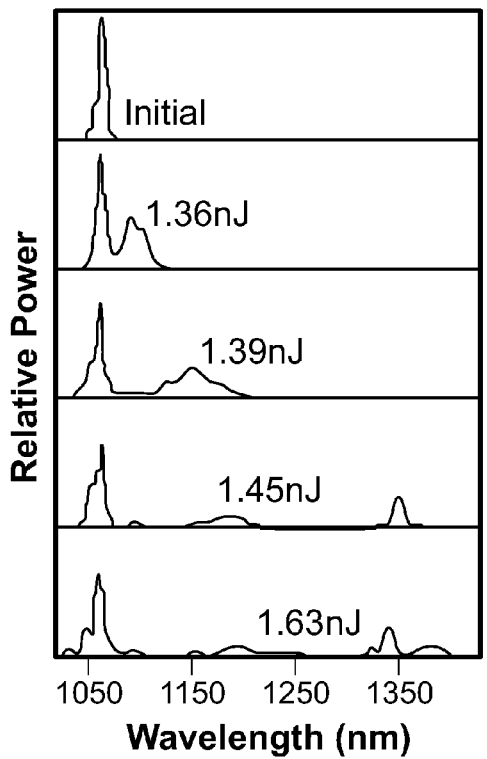
FIG. 2A is a graph of soliton self-frequency shifted spectra corresponding to different input pulse energies into the HOM fiber of FIG. 1C.
Figure 2B:
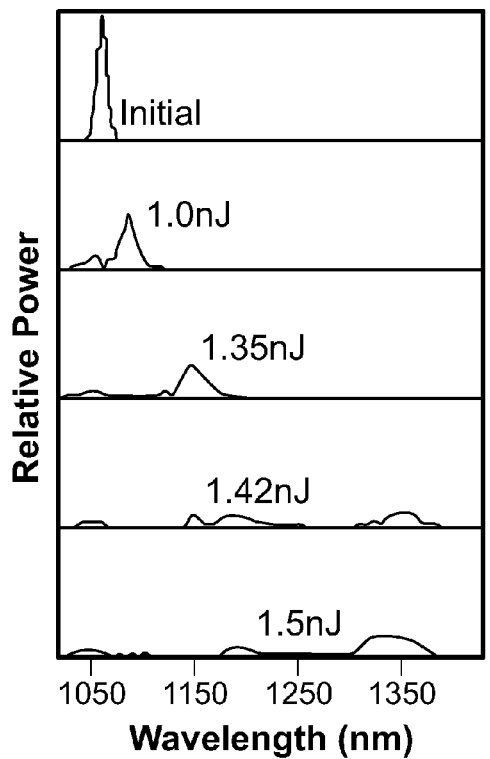
FIG. 2B is a graph of soliton self-frequency shifted spectra calculated from simulation using a 200 fs input Gaussian pulse and input pulse energies comparable to those in FIG. 2A.

In FIG. 1C, the pump source 102 includes a fiber laser (a Fianium FP1060-1S in this example) delivering a free space output of 200 fs pulses at a center wavelength of 1064 nm and an 80 MHz repetition rate. A maximum power of 130 mW is coupled into the HOM fiber module corresponding to 1.63 nJ input pulses. Using a variable attenuator, the input pulse energy is varied from 1.36 nJ to 1.63 nJ to obtain clean spectrally-shifted solitons with a maximum wavelength shift of 136 nm (12% of the carrier wavelength) as shown in FIG. 2A. In FIG. 2A, all the traces are taken at 4.0 nm resolution bandwidth (RBW). Input pulse energy is noted on each trace in FIGS. 2A-2B. Power conversion efficiency is 57% for 1.39 nJ input. Theoretical traces from numerical simulation for similar input pulse energy are plotted adjacent to the experimental data in FIG. 2B. The split-step Fourier method was used in the simulation and included self-phase modulation (SPM), stimulated Raman scattering (SRS), self-steepening, and dispersion up to fifth-order. FIG. 2B is a graph of soliton self-frequency shifted spectra calculated from simulation using a 200 fs input Gaussian pulse and shifted soliton energies comparable to those in FIG. 2A. A nonlinear parameter $\gamma=2.2\, W^{-1}\, Km^{-1}$ and a Raman response of $T_R=5$ fs were used. (Agrawal, G. P., *Nonlinear Fiber Optics*, Third ed., Academic Press: San Diego (2001) which is hereby incorporated by reference in its entirety). Though a more accurate description may include the full integral form of the nonlinear Schrödinger equation (Agrawal, G. P., *Nonlinear Fiber Optics*, Third ed., Academic Press: San Diego (2001), which is hereby incorporated by reference in its entirety), the excellent qualitative match and reasonable quantitative match is obtained with this approach.

Figure 3:
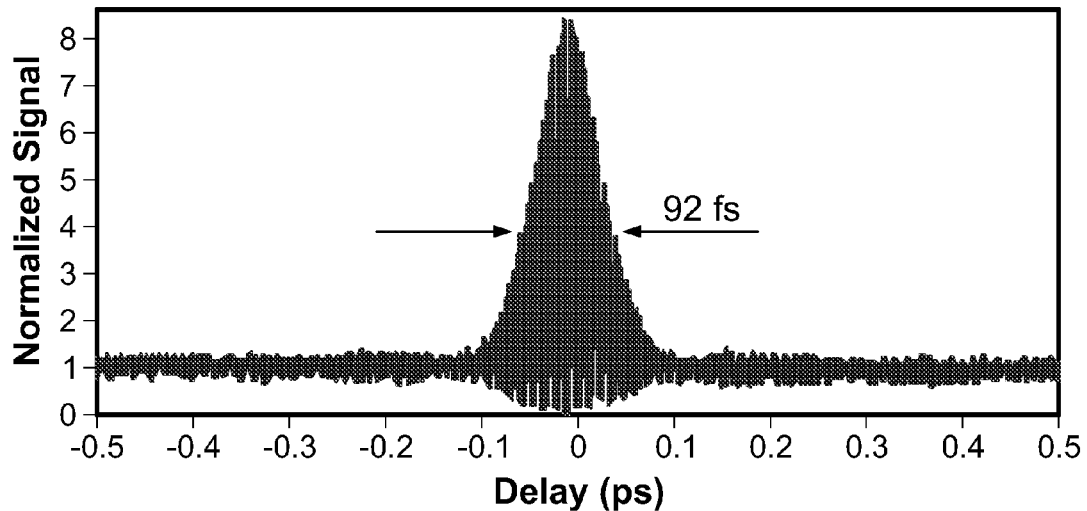
FIG. 3 is a second-order interferometric autocorrelation trace of the HOM fiber output for 1.39 nJ input pulses.

A 57% power conversion from the input pulse spectrum to the red-shifted soliton was measured for the case of 1.39 nJ input pulses to achieve approximately 0.8 nJ output soliton pulses as shown in FIG. 2A. FIG. 3 is a second-order interferometric autocorrelation trace of the HOM fiber output for 1.39 nJ input pulses. The corresponding second-order interferometric autocorrelation as shown in FIG. 3 gives an output pulse width of 49 fs, assuming a sech pulse shape, showing a factor of four in pulse width reduction due to higher order soliton compression (soliton order N=2.1) in the HOM fiber 110. The measured spectral bandwidth of 35 nm gives a time-bandwidth product of 0.386 which is 23% beyond that expected for a sech² pulse shape. The discrepancy is likely due to dispersion from the approximately 5 cm of glass (the coupling and focusing lenses 104 and 115 in FIG. 2C of this example) between the fiber output and the two-photon detector inside the autocorrelator coupled to the interface 116. This is supported by numerical simulation which gives an output pulse width of 40 fs.

Light can be easily coupled back into the fundamental mode using another LPG at the output end of the system 100 in FIG. 1C. By using a dispersion-matching design, ultra-large bandwidths can be supported by a LPG (Ramachandran, S., *Journal of Lightwave Technology* 23:3426 (2005), which is hereby incorporated by reference in its entirety). Conversion efficiency of 90% over a bandwidth of 200 nm is obtained for a similar fiber structure (Ramachandran et al., *Opt. Lett.* 31:1797 (2006), which is hereby incorporated by reference in its entirety). Such a LPG will ensure the output pulse is always converted back to a Gaussian profile, within the tuning range.

Both the wavelength shift and pulse energy can be significantly increased beyond what has been demonstrated through engineering of the fiber module. For example, simple dimensional scaling of the index profile can be used to shift the dispersion curve of the $LP_{02}$ mode. Numerical modeling shows that an output soliton energy of approximately 2 nJ can be realized if the dispersion curve is shifted approximately 100 nm to the longer wavelength side. Additionally, pulse energy can be scaled by increasing $D \cdot A_{eff}$. Aside from increasing the magnitude of dispersion through manipulation of the index profile and dimensions of the fiber, the effective area can be significantly enhanced by coupling into even higher order modes. An effective area of approximately 2000 μm² (more than 40 times this HOM fiber) was recently achieved by coupling to the $LP_{07}$ mode (Ramachandran et al., *Opt. Lett.* 31:1797 (2006), which is hereby incorporated by reference in its entirety).

In summary, soliton self-frequency shift between 1064 nm and 1200 nm is demonstrated in a higher order mode, solid silica-based fiber such as the HOM fiber 110 in FIG. 1C. 49 fs Raman-shifted solitons are obtainable at 0.8 nJ with up to 57% power conversion efficiency. Due to the dispersion characteristics of the HOM fiber, Cherenkov radiation is observed for appropriately energetic input pulses. The HOM fiber provides an ideal platform for achieving soliton energies from 1 to 10 nJ for soliton self-frequency shift at wavelengths below 1300 nm, filling the pulse energy gap between index-guided photonic crystal fibers and air-core photonic band-gap fibers. This intermediate pulse energy regime which could not be reached previously for soliton self-frequency shift is instrumental in the realization of tunable, compact, all-fiber, femtosecond sources for a wide range of practical applications.

In addition, soliton self-frequency shift below 1300 nm in a 240 nm range between 1064 nm and 1300 nm is demonstrated in a higher order mode, solid silica-based fiber such as HOM fiber 110 at soliton energies above 1.0 nJ. In this example, the dispersion has an effective area of 70 μm² and dispersion-zeros separated by 415 nm.

Preliminary Studies

Figure 4:
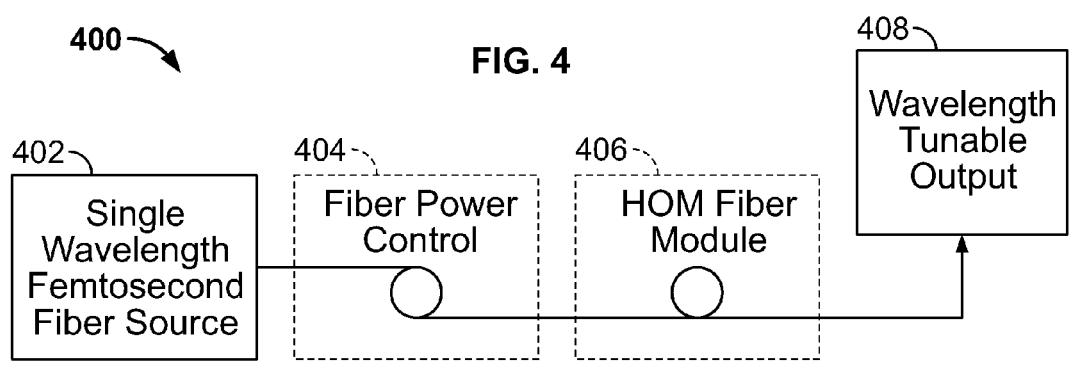
FIG. 4 is a schematic drawing of one embodiment of an all fiber, wavelength tunable, energetic, femtosecond source.

The example sources allow generating energetic femtosecond pulses that are continuously tunable across a wide wavelength range, where, in contrast to previous approaches, ultrafast pulses are wavelength shifted in the novel higher order mode (HOM) fiber module by soliton self-frequency shift. By eliminating the constraint of a broad gain medium to cover the entire tuning range, this approach allows rapid, electronically controlled wavelength tuning of energetic pulses in an all-fiber configuration. FIG. 4 schematically shows the design of an example excitation source system 400. The system 400 includes a single wavelength femtosecond fiber source 402, a fiber power control 404, a HOM fiber module 406 and a wavelength tunable output 408. The single wavelength femtosecond fiber source 402 is at 1030 nm (or 775 nm with frequency doubling from 1550 nm) with high pulse energy (10 to 25 nJ). The pulse is then propagated into the specifically designed HOM fiber module 406 for wavelength shifting via soliton self-frequency shift. The output wavelength of the soliton pulses are controlled by the input pulse energies (and/or HOM fiber length). The target performance of the system 500 are 5 to 10 nJ pulses tunable from (1) 775 to 1000 nm and (2) 1030 to 1280 nm in an all-fiber configuration. Data relating to the femtosecond fiber sources, HOM fibers, and soliton self-frequency shift, three key components of the femtosecond source, are described below.

Design Simulations

Figure 5A:
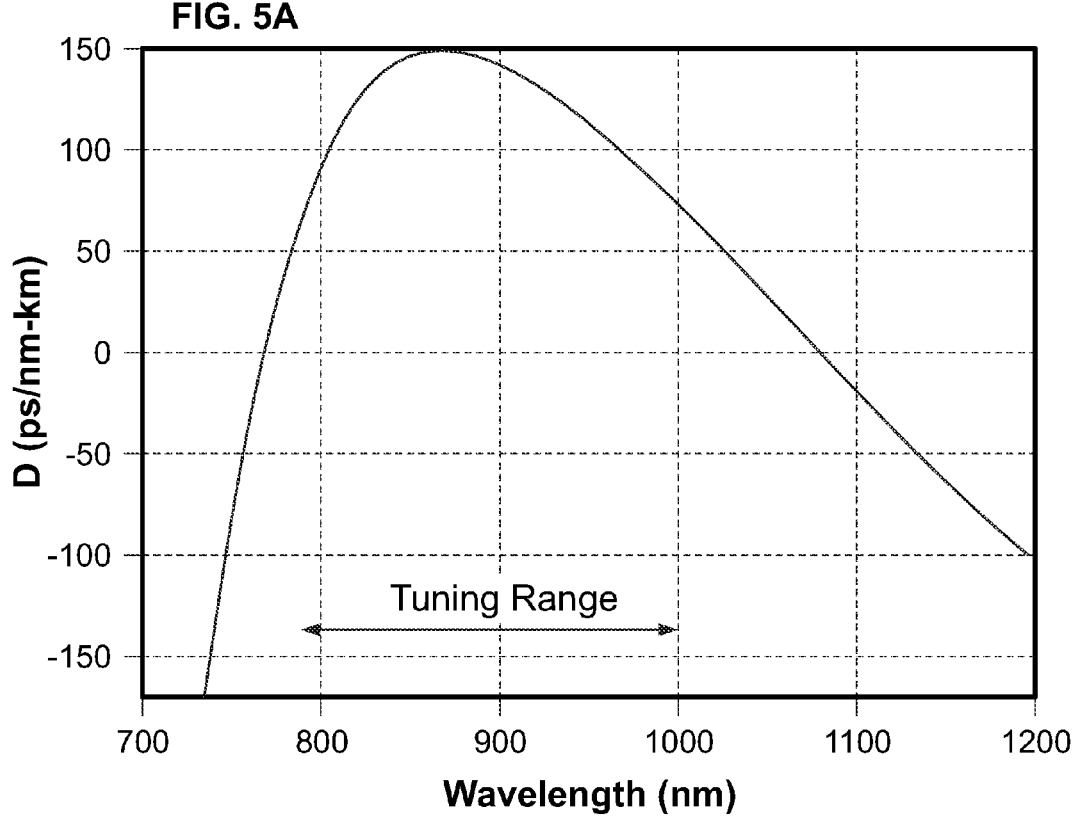
FIG. 5A shows designed dispersion (D) versus wavelength curves for wavelength tuning at a 775 nm input.
Figure 5B:
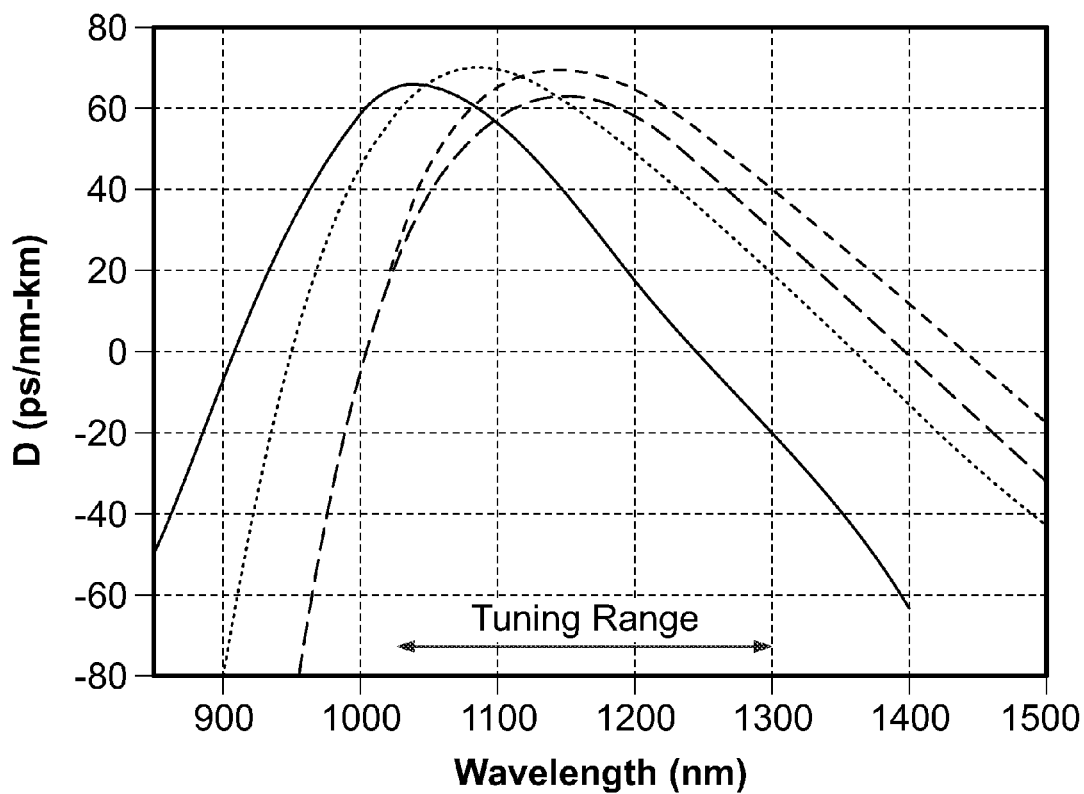
FIG. 5B shows designed dispersion (D) versus wavelength curves for wavelength tuning at a 1030 nm input.
Figure 6A:
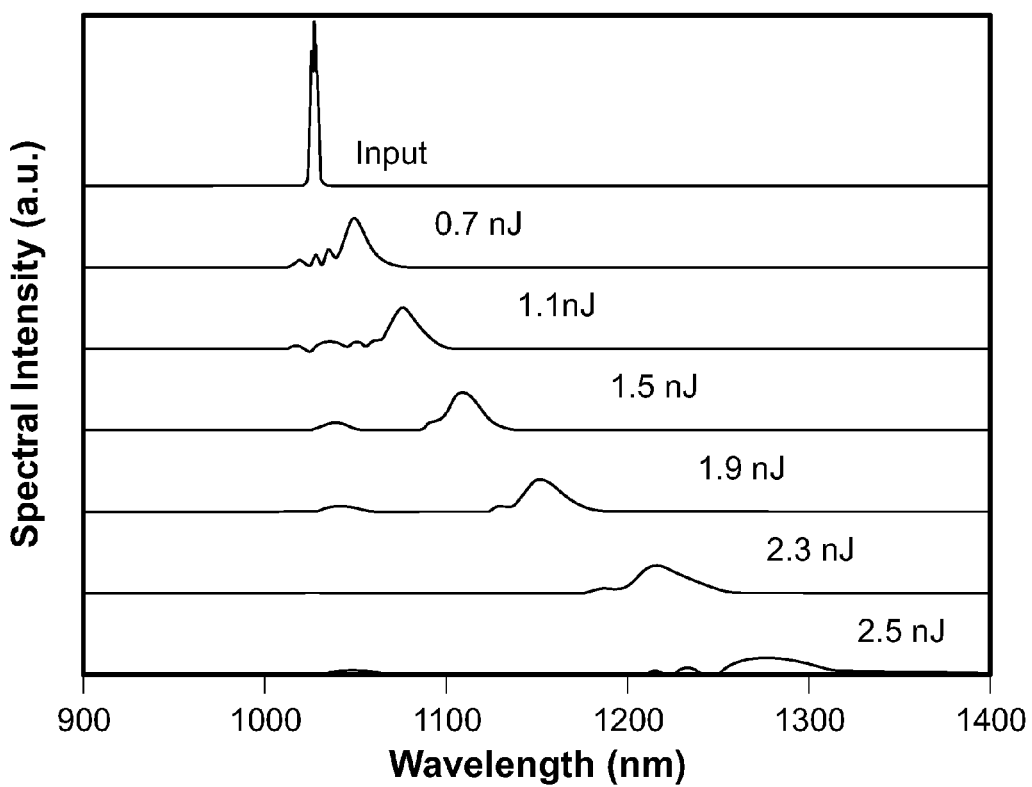
FIG. 6A shows output spectra at various input pulse energies for a 1 meter HOM fiber.
Figure 6B:
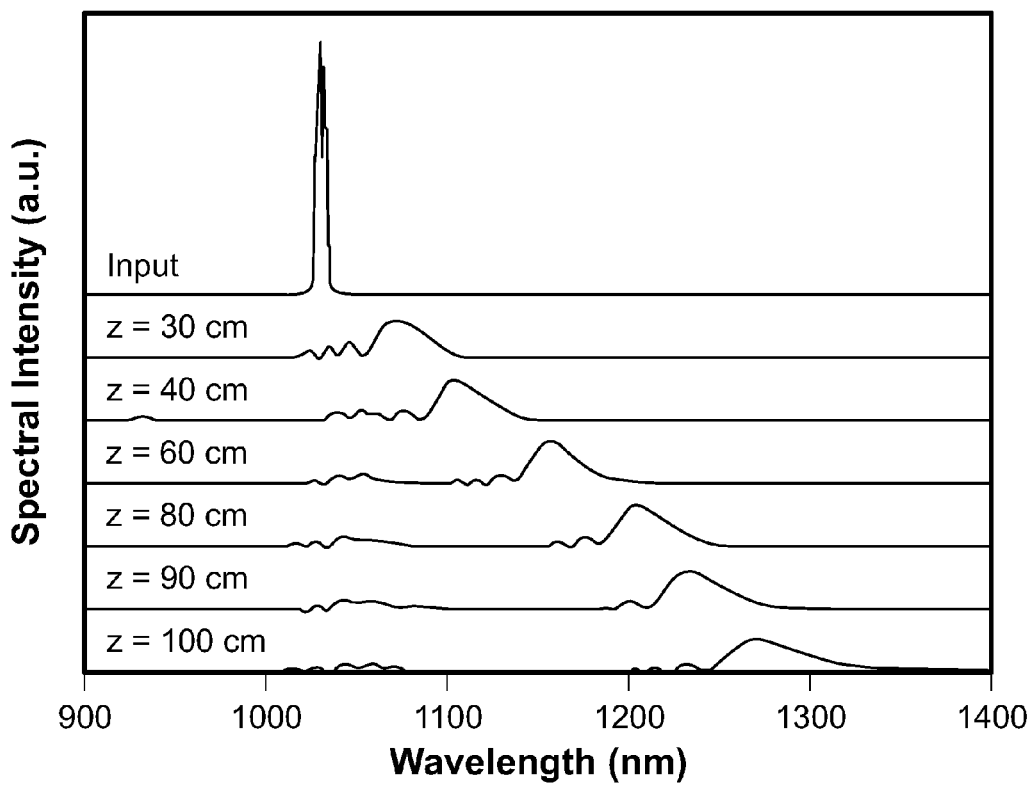
FIG. 6B shows output spectra at various propagation distance (z) in the HOM fiber (i.e., HOM fiber length) for an input pulse energy of 2.5 nJ.

Through extensive numerical simulations, the required dispersion is shown in FIG. 5A and the effective area, $A_{eff}$ of the HOM fibers to achieve 1 to 2 nJ pulses, tunable from 775 to 1000 nm and 1030 to 1280 nm. In FIGS. 5A-5B, the calculated wavelength tuning range is indicated. The existing HOM fiber is also indicated as a solid line in FIG. 5B. FIG. 5A shows designed dispersion (D) versus wavelength curves for wavelength tuning at 775 nm input while FIG. 5B shows designed dispersion (D) versus wavelength curves for wavelength tuning at 1030 nm input. FIG. 6A shows numerical simulation results of SSFS in such HOM fibers, by adjusting the launch power into the HOM fiber module. FIG. 6A shows output spectra at various input pulse energies for a 1 meter HOM fiber and FIG. 6B shows output spectra at various propagation distance (z) in the HOM fiber (i.e., HOM fiber length) for an input pulse energy of 2.5 nJ. For comparison, the input spectrum is also shown in FIGS. 6A and 6B. Each spectrum has been vertically offset so that all of them may be displayed on the same plot in FIGS. 6A and 6B. The conversion efficiency is approximately 70% for a Gaussian input pulse at 280 fs width (FWHM). Thus, even a 5 nJ pulse launched into the HOM fiber module is sufficient to achieve the design specifications. The output pulse widths are between 50 and 70 fs throughout the tuning range. Very similar results were also obtained for the 775 nm input with the design curve shown in FIG. 5A. A shift as large as approximately 50 nm in zero-dispersion wavelength (the dash-dotted and the dotted line in FIG. 5B) will not significantly impact (<8% in output pulse energy) the performance of the HOM fiber, making the design tolerant to fabrication imperfections.

In addition to the power tuning of the output wavelength, an alternative method for wavelength tuning is simply using different fiber length. FIG. 6B shows the simulated output spectrum at various HOM fiber lengths while maintaining the input power. Tuning range identical to using power adjustment, with a conversion efficiency of approximately 70%, can be easily achieved.

System Demonstration.

Second harmonic generation (SHG) may be employed to generate femtosecond pulses at 775 nm. Systems are designed using two different tuning mechanisms, power tuning and length tuning. As shown in the results, both tuning mechanisms offer similar tuning range as shown in FIGS. 6A-6B. The power tuning requires only one HOM fiber module for the entire spectral range, however, the output power varies by approximately a factor of 3 (power input multiplied by the conversion efficiency). Although such power variation across the tuning range is comparable to current femtosecond systems like the Ti:S or Ti:S pumped optical parametric oscillator (OPO), it may nonetheless limit the practical utility of the system, particularly at the smaller wavelength shift where the output power is the lowest. Another tuning approach is fiber length tuning, which can essentially maintain the output power as shown in FIG. 6B, within +/−5% across the entire spectral range. Fiber length tuning requires multiple HOM fiber modules, increasing the system cost. The two tuning mechanisms may be combined. As an alternative to power tuning, HOM fiber modules of different length may be provided. Each different length HOM fiber module is optimized for power tuning over an approximate 100 nm spectral range to maintain a reasonably constant output. Such segmented tuning also simplifies the design of the output LPGs since a much narrower range of output wavelengths needs to be converted. Such segmented tuning is similar to the early generations of Ti:S lasers where multiple mirror sets were required to cover the entire tuning range. However, unlike a mirror-set exchange in a Ti:S laser, which takes an experienced operator several hours to perform, the exchange of the HOM fiber modules takes only a few seconds to connect the desired HOM fiber module to the single wavelength fiber source through a single mode fiber connector and require neither experience nor knowledge of the system. For a completely electronically controlled system, a simple fiber optic switch may be used to provide push-button HOM fiber module exchange. In fact, such a tunable HOM fiber module is available for telecom applications.

Both power tuning and segmented length tuning require a mechanism to control the incident power. SSFS is a nonlinear optical effect and effectively happens instantaneously (<1 ps). Thus, the rate of the wavelength tuning of the fiber source may be ultrafast, and is completely determined by the rate of power change. There are two approaches to adjust the power into the HOM fiber module. Mechanical in-line fiber attenuators can achieve a tuning speed of approximately 10 Hz, several orders of magnitude faster than any existing laser systems. Because only a small range of power adjustment is necessary for achieving the entire range of wavelength tuning (less than a factor of 4 for power tuning), variable fiber attenuators that based on microbending may easily provide the speed and modulation depth required. Such a variable attenuator may be calibrated so that rapid, electronically controlled wavelength tuning can be achieved. Compact, electronically controlled variable fiber attenuators are widely available. Most attenuators provide modulation depth of approximately 1000 and thus the power control mechanism may be implemented without difficulty. An alternative approach is a fiber coupled electro-optic modulator (EOM). Although such an approach will be more expensive, it can easily provide nanosecond (i.e., pulse-to-pulse) wavelength switching speed. In addition, such a device also provides the capability for fast (ns) laser intensity control. To overcome the insertion loss of the electro-optic modulator, the EOM may be placed before the fiber amplifier in a CPA system. These EOMs are routinely used in telecommunications and are highly robust (telecom certified) and compact (the size of half a candy bar). The source in FIG. 4 may be readily configured to provide this high speed tuning capability.

The SSFS is a nonlinear optical effect and as such is generally sensitive to fluctuations in input power, pulse width, and pulse spectrum. An all-fiber, single wavelength femtosecond source is used. One of the salient features of an all-fiber design is its stability. It is well known that a fiber laser is more stable than a bulk solid state laser. The fiber sources are specifically designed for biomedical imaging applications in this example, although it is to be understood that other applications may use the principles described herein. Because of the broad output pulse spectrum (10 to 20 nm) and the broad excitation peaks of fluorescent molecules (tens of nm), a few nm of wavelength shift is generally inconsequential. This is in sharp contrast to applications such as precision frequency metrology, where even a small fraction of an Angstrom spectral shift cannot be tolerated. Finally, the soliton pulse shaping process is robust against fluctuations in the input, which is one of the main reasons that solitons were used in long haul communication systems. FIG. 3 also clearly demonstrates the robustness of SSFS. Even with a highly non-ideal input pulse, a nearly perfect soliton pulse is obtained at the output as shown in FIG. 3. In addition, simulations with a perfect Gaussian pulse input showed good agreement with the experiments, particularly for the output at the soliton wavelength. In the unlikely event that unacceptably large power fluctuations are present, an alternative approach is to employ feedback stabilization. Because power adjustment mechanisms are already needed for wavelength tuning, the only additional component for feedback control is a photodiode for power monitoring (for example, through a 1% fiber tap in the single mode pigtail fiber 106 before the LPG 108 in FIG. 1C). Such a feedback control mechanism can largely eliminate power drifts on the slow time scale, approximately 10 Hz for the mechanical variable fiber attenuator and approximately 1 MHz for the electro-optical intensity modulator. A power stabilization scheme ("noise eater") has already been commercially implemented for a variety of laser systems.

Polarization control is another issue of practical concern. For applications that demand a linear input polarization, polarization maintaining fibers may be used throughout the system. Because the HOM fiber is fabricated within the conventional silica fiber platform, polarization maintaining HOM fibers may be made using the same method designed for conventional polarization maintaining fibers (such as adding stress rods to form a Panda fiber). For applications that demand adjustable input polarization, non-polarization maintaining HOM fibers can be used and a simple in-line fiber polarization controller can be used to adjust the output polarization state, eliminating the conventional free-space wave plate and/or polarizer.

There are several methods to remove the residue input light at the output of the HOM fiber module. Perhaps the simplest approach is to directly deposit a dichroic coating (long wavelength pass) on the output face of the fiber since a silica fiber is a piece of glass with a small diameter. Such coatings are often applied for fiber lasers with linear cavities and the deposition techniques are similar to that on a conventional glass substrate.

Biomedical Applications.

The new femtosecond laser sources may be applied to biomedical applications such as multiphoton microscopy, spectroscopy and endoscopy.

Figure 7:
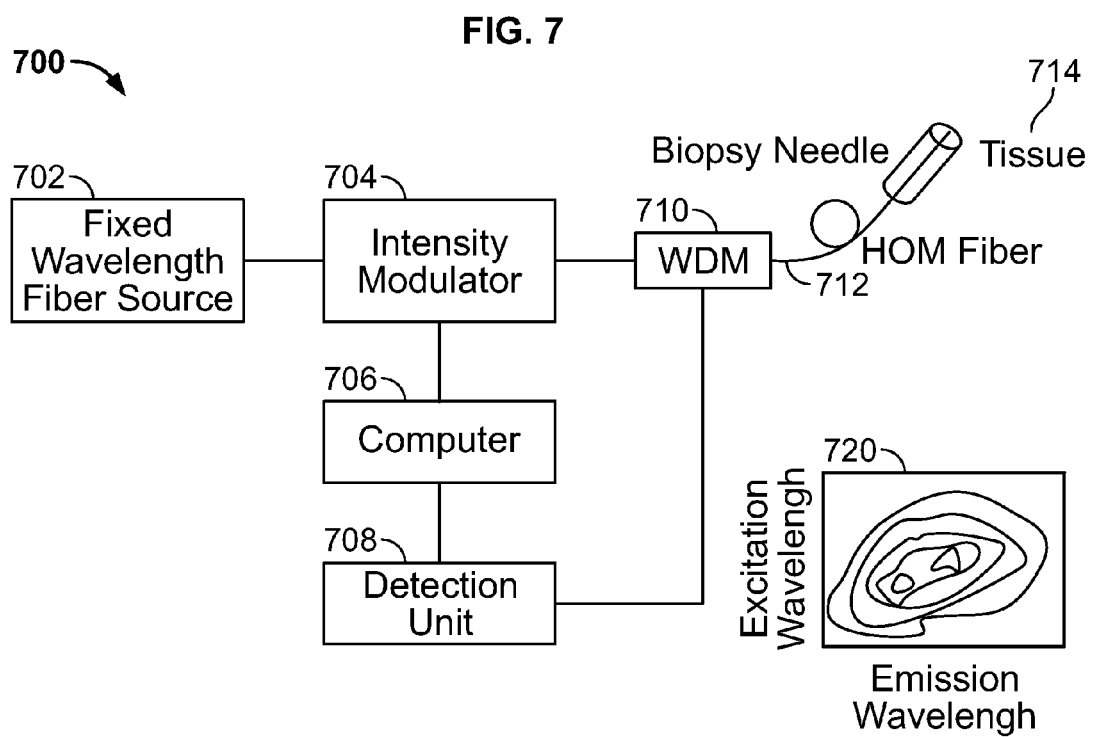
FIG. 7 is a block diagram of an example instrument system for multiphoton spectroscopy on cancer tissues.

The HOM fiber that provides wavelength tuning through SSFS may be simultaneously used as the delivery and collection fiber for tissue spectroscopy. The diameter of the optical fiber in this example is approximately 0.125 mm (the standard size for a single mode fiber), which is much smaller than the inside diameter of an 18 or 20 gauge needle that is routinely used for core biopsy. The excited signal is collected by the same fiber. A fiber wavelength division multiplexer (WDM) can be placed between the fixed wavelength femtosecond source and the HOM fiber module to direct the collected signal to the detecting unit, which consists a grating and a charge coupled device (CCD). In addition, the rapid wavelength tuning capability allows the emission spectrum of the tissue to be recorded as a function of the excitation wavelength. These multiphoton excited fluorescence excitation-emission matrix (EEM) can potentially provide unique diagnostic signatures for cancer detection just as a one-photon EEM does. FIG. 7 is a block diagram of an all-fiber, multiphoton excited needle biopsy system 700. The system 700 includes a fixed wavelength fiber source 702, an intensity modulator 704, a computer 706, a detection unit 708, and a wavelength division multiplexer (WDM) 710. A HOM fiber 712 is coupled to the WDM 710 and a biopsy needle 714. The biopsy needle 714 is inserted in tissue 716. An inset 720 shows a schematic contour plot of the excitation-emission matrix (EEM). A double-clad fiber structure with the HOM fiber as the guiding core may be easily fabricated to improve signal collection efficiency because of the all-silica fiber design.

One potential complication of the proposed tunable source for multiphoton EEM is the power and pulse width variation across the entire tuning range. Calibration using a known multiphoton excitation standard, such as fluorescein dye, is carried out before experimentation on biological samples. Such a calibration procedure is routinely used in previous multiphoton spectroscopy work.

Rapid, Electronically Controlled Wavelength Tuning.

A unique capability of the sources disclosed is the ability to rapidly tune the wavelength much faster than currently possible with single box Ti:S systems. Rapid wavelength tuning allows for line by line switching between excitation wavelengths during scanning, or for collecting excitation spectra, an important parameter for biomedical applications that may utilize intrinsic fluorophores with overlapping emissions, but differing excitation spectra.

By synchronizing the wavelength control with the scanning and acquisition, an imaging system may be modified to enable one wavelength during the "forward" line and a second wavelength during the return (without changing the Y position). This is analogous to what is now standard on modern AOM-equipped confocal microscopes, where, for example, a green dye is excited with 488 nm excitation in one direction and 547 nm excitation to excite a different dye during the return. In this way a two-color image may be collected using dyes with different excitation maximums and separable emissions. The temporal aspect eliminates problems with spectral cross-talk in many cases. Although multiphoton cross-sections for many dyes are broad often allowing for excitation of different dyes at the same wavelength (usually due to overlapping UV bands, so this normally only works at 800 nm or shorter), the ability to rapidly switch between wavelengths anywhere between 780 and 1000 nm may be an important enhancement for many dyes pairs. After interfacing the wavelength control with the scanning system 700, this capability may be demonstrated with fluorophores such as CFP and GFP which have different two photon excitation maxima, but partially overlapping emission spectra. FIG. 8A shows a two-photon excitation spectra of CFP and monomeric eGFP, two common genetically encodable fluorescent proteins and FIG. 8B shows emission spectra of the CFP and monomeric eGFP.

As an added benefit, the EOM device that enables rapid wavelength tuning can also be used to provide fast switching and modulation of the excitation beam. At a minimum this functionality should be comparable to what is currently achieved using 80-mm resonance-dampened KTP* Pockel cells for routine beam blanking and intensity control (microsecond switching). Available fiber-coupled EOMs can switch in the sub-nanosecond range and allow for a laser with a built-in modulator that enables a user to reduce the effective laser repetition rate for measurements of fluorescent decays times and fluorescent lifetime imaging (FLIM), as well as for the more standard modulation needs. The required control electronics may be implemented for providing routine beam blanking and control, photobleaching recovery measurements, and FLIM.

Soliton self-frequency shift in a HOM fiber also allows multiple wavelength tunable pulses to be obtained from the same fixed wavelength fiber source. For example, the output of the fixed wavelength femtosecond fiber source may be split into two halves and each half propagates through a HOM fiber module such as that in FIG. 1C. The two HOM fiber modules may be the same (using power tuning) or of different lengths (using length tuning) Such a multi-color femtosecond source opens a range of new applications, such as two-color two-photon excitation and coherent anti-Stokes Raman scattering (CARS) imaging, where two synchronized ultrafast sources are needed previously. The spectral bandwidths directly from the proposed sources may possibly requiring spectral filtering or shaping for CARS imaging.

The use of SSFS in HOM fiber offers unprecedented capability at the wavelength window of 1030 to 1280 nm. For example, longer wavelength multiphoton imaging beyond 1100 nm is feasible and offers significant advantages in deep tissue imaging, particularly with the high pulse energy from the example source. Applications of the new spectral window may be made for multiphoton microscopes and endoscopes. Unprecedented imaging depth using the energetic pulses from the example source may be achieved. The all-fiber, wavelength tunable, energetic femtosecond source at the longer wavelength window of 1030 to 1280 nm opens significant new opportunities for biomedical imaging.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An apparatus for producing optical pulses of a desired wavelength, said apparatus comprising:
    an optical pulse source operable to generate optical pulses at a first wavelength that is below 1300 nanometers (nm); and
    a higher order mode (HOM) fiber module including an HOM fiber, optically coupled to the optical pulse source so as to receive the optical pulses at the first wavelength, wherein the HOM fiber is characterized to provide anomalous dispersion at the first wavelength so as to produce output optical pulses at the desired wavelength that is different than the first wavelength by soliton self-frequency shift (SSFS) in the HOM fiber, wherein the desired wavelength is below 1300 nm.

2. The apparatus according to claim 1, wherein the HOM fiber is a solid silica-based fiber.

3. The apparatus according to claim 1, wherein the HOM fiber module includes an HOM fiber and at least one mode converter.

4. The apparatus according to claim 3, wherein the at least one mode converter is connectedly disposed between the optical pulse source and the HOM fiber.

5. The apparatus according to claim 4 further comprising: a second mode converter terminally connected to the HOM fiber.

6. The apparatus according to claim 3, wherein the at least one mode converter is a long period grating (LPG).

7. The apparatus according to claim 1, wherein the optical pulse source generates input optical pulses having a pulse energy of at least 1.0 nanojoule (nJ).

8. The apparatus according to claim 1, wherein the optical pulse source generates input optical pulses having a pulse energy of between about 1.0 nJ and about 10 nJ.

9. The apparatus according to claim 1, wherein the optical pulse source comprises either a mode-locked laser or a chirped pulse amplification (CPA) system.

10. The apparatus according to claim 9, wherein the mode-locked laser is a mode-locked fiber laser.

11. The apparatus according to claim 9, wherein the CPA system is a fiber CPA system.

12. The apparatus according to claim 1, wherein the optical pulse source generates input optical pulses such that the first wavelength is a wavelength within the transparent region of a silica-based fiber.

13. The apparatus according to claim 1, wherein the first wavelength is a wavelength between the range of about 300 nm and about 1300 nm.

14. The apparatus according to claim 1, wherein the optical pulse source generates input optical pulses having a subpicosecond pulse width.

15. The apparatus according to claim 1, wherein the HOM fiber module produces output optical pulses having a pulse energy of at least 1.0 nJ.

16. The apparatus according to claim 1, wherein the HOM fiber module produces output optical pulses such that the desired wavelength is a wavelength within the transparent region of a silica-based fiber.

17. The apparatus according to claim 1, wherein the desired wavelength is a wavelength between the range of about 300 nm and about 1300 nm.

18. The apparatus according to claim 1, wherein the HOM fiber module produces output optical pulses having a subpicosecond pulse width.

19. The apparatus according to claim 1 further comprising: a power control system connectedly disposed between the optical pulse source and the HOM fiber module.

20. The apparatus according to claim 19, wherein the power control system achieves subnanosecond power tuning of the first wavelength.

21. The apparatus according to claim 20, wherein the power control system comprises a lithium niobate intensity modulator device.

22. The apparatus according to claim 1, further comprising a length tuning system that varies the length of the HOM fiber to the first wavelength.

23. The apparatus according to claim 1 further comprising: a single-mode fiber (SMF) connectedly disposed between the optical pulse source and the HOM fiber module.

24. The apparatus according to claim 1, wherein the HOM fiber module produces output optical pulses that can penetrate animal or plant tissue at a penetration depth of at least 0.1 millimeters (mm).

25. The apparatus according to claim 1 further comprising: an endoscope terminally associated with the HOM fiber module.

26. The apparatus according to claim 1 further comprising: an optical biopsy needle terminally associated with the HOM fiber module.

27. The apparatus according to claim 1 further comprising: a multiphoton microscope system functionally associated with the apparatus.

28. The apparatus according to claim 1 further comprising: a multiphoton imaging system functionally associated with the apparatus.

29. A method of producing optical pulses having a desired wavelength, said method comprising:
generating optical pulses from an optical pulse source, wherein the optical pulses have a first wavelength that is below 1300 nanometers (nm) and a first spatial mode; and
inputting the optical pulses to a higher order mode (HOM) fiber, wherein the HOM fiber is characterized to provide anomalous dispersion at the first wavelength so as to alter the wavelength of the optical pulses from the first wavelength to a desired wavelength that is different than the first wavelength by soliton self-frequency shift (SSFS) within the HOM fiber, thereby producing output optical pulses having the desired second wavelength, wherein the desired wavelength is below 1300 nm.

30. The method according to claim 29, wherein the HOM fiber is a solid silica-based fiber.

31. The method according to claim 29 further comprising: converting the first spatial mode of the input optical pulses into a second spatial mode prior delivering the input optical pulses into the HOM fiber so that the output optical pulses have the second spatial mode, wherein the first spatial mode and the second spatial mode are different modes.

32. The method according to claim 31 further comprising: reconverting the second spatial mode of the output optical pulses back to the first spatial mode.

33. The method according to claim 29, wherein the optical pulse source generates input optical pulses having a pulse energy of at least 1.0 nanojoule (nJ).

34. The method according to claim 29, wherein the optical pulse source generates input optical pulses having a pulse energy of between about 1.0 nJ and about 10 nJ.

35. The method according to claim 29, wherein the optical pulse source comprises either a mode-locked laser or a chirped pulse amplification (CPA) system.

36. The method according to claim 35, wherein the mode-locked laser is a mode-locked fiber laser.

37. The method according to claim 35, wherein the CPA system is a fiber CPA system.

38. The method according to claim 29, wherein the optical pulse source generates input optical pulses such that the first wavelength is a wavelength within the transparent region of a silica-based fiber.

39. The method according to claim 29, wherein the first wavelength is a wavelength between the range of about 300 nm and about 1300 nm.

40. The method according to claim 29, wherein the optical pulse source generates input optical pulses having a subpicosecond pulse width.

41. The method according to claim 29, wherein the HOM fiber module produces output optical pulses having a pulse energy of at least 1.0 nJ.

42. The method according to claim 29, wherein the HOM fiber module produces output optical pulses such that the desired wavelength is a wavelength within the transparent region of a silica-based fiber.

43. The method according to claim 29, wherein the desired wavelength is a wavelength between the range of about 300 nm and about 1300 nm.

44. The method according to claim 29, wherein the HOM fiber module produces output optical pulses having a subpicosecond pulse width.

45. The method according to claim 29 further comprising:
tuning the first wavelength of the input optical pulses to an intermediate wavelength prior to delivering the input optical pulses into the HOM fiber.

46. The method according to claim 45, wherein the tuning comprises subnanosecond power tuning using a power control system connectedly disposed between the optical pulse source and the HOM fiber module.

47. The method according to claim 46, wherein the power control system is a lithium niobate intensity modulator device.

48. The method according to claim 29 further comprising:
varying the length of the HOM fiber so as to vary the desired wavelength.

49. The method according to claim 29 further comprising:
varying the power of the input optical pulses so as to vary the desired wavelength.

* * * * *